(12) United States Patent
Park et al.

(10) Patent No.: US 8,656,323 B2
(45) Date of Patent: Feb. 18, 2014

(54) BASED DEVICE RISK ASSESSMENT

(75) Inventors: Allen Park, San Jose, CA (US);
Youseung Jin, Hwasung (KR);
SungChan Cho, Hwasung-Si (KR);
Barry Saville, Gansevoort, NY (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/399,805

(22) Filed: Feb. 17, 2012

(65) Prior Publication Data
US 2012/0216169 A1 Aug. 23, 2012

Related U.S. Application Data

(60) Provisional application No. 61/445,164, filed on Feb. 22, 2011.

(51) Int. Cl.
*G06F 17/50* (2006.01)
(52) U.S. Cl.
USPC ............... 716/56; 716/50; 716/51; 716/52
(58) Field of Classification Search
None
See application file for complete search history.

(56) References Cited

U.S. PATENT DOCUMENTS

| | | | | |
|---|---|---|---|---|
| 4,475,122 A * | 10/1984 | Green | | 348/87 |
| 6,470,489 B1 * | 10/2002 | Chang et al. | | 716/52 |
| 6,775,817 B2 * | 8/2004 | Ono et al. | | 716/52 |
| 7,003,758 B2 * | 2/2006 | Ye et al. | | 716/52 |
| 7,120,895 B2 * | 10/2006 | Ye et al. | | 716/51 |
| 7,394,534 B1 | 7/2008 | Huet et al. | | |
| 7,570,796 B2 * | 8/2009 | Zafar et al. | | 382/144 |
| 7,600,212 B2 * | 10/2009 | Zach et al. | | 716/50 |
| 7,698,676 B1 * | 4/2010 | Qian | | 716/119 |
| 7,975,245 B2 * | 7/2011 | Florence et al. | | 716/52 |
| 8,041,103 B2 * | 10/2011 | Kulkarni et al. | | 382/144 |
| 8,139,843 B2 * | 3/2012 | Kulkarni et al. | | 382/144 |
| 8,151,234 B2 * | 4/2012 | Berkens et al. | | 716/119 |
| 2002/0010560 A1 * | 1/2002 | Balachandran | | 702/118 |
| 2006/0066339 A1 * | 3/2006 | Rajski et al. | | 324/765 |
| 2008/0250361 A1 | 10/2008 | Bae et al. | | |
| 2009/0007030 A1 * | 1/2009 | Nehmadi et al. | | 716/4 |
| 2009/0055783 A1 | 2/2009 | Florence et al. | | |
| 2009/0297019 A1 * | 12/2009 | Zafar et al. | | 382/145 |
| 2011/0286656 A1 * | 11/2011 | Kulkarni et al. | | 382/144 |
| 2012/0216169 A1 * | 8/2012 | Park et al. | | 716/136 |

* cited by examiner

*Primary Examiner* — A. M. Thompson
(74) *Attorney, Agent, or Firm* — Suiter Swantz pc llo

(57) ABSTRACT

The process for designed based assessment includes the following steps. First, the process defines multiple patterns of interest (POIs) utilizing design data of a device and then generates a design based classification database. Further, the process receives one or more inspection results. Then, the process compares the inspection results to each of the plurality of POIs in order to identify occurrences of the POIs in the inspection results. In turn, the process determines yield impact of each POI utilizing process yield data and monitors a frequency of occurrence of each of the POIs and the criticality of the POIs in order to identify process excursions of the device. Finally, the process determines a device risk level by calculating a normalized polygon frequency for the device utilizing a frequency of occurrence for each of the critical polygons and a criticality for each of the critical polygons.

4 Claims, 10 Drawing Sheets

BASED DEVICE RISK ASSESSMENT

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional patent application entitled DESIGN-AWARE DEVICE ASSESSMENT AND COMPUTER-AIDED SEPARATION OF PARTICLE AND PATTERN DEFECT, naming Allen Park, Youseung Jin, Barry Saville, and Sungchan Cho as inventors, filed Feb. 22, 2011, Application Ser. No. 61/445,164.

TECHNICAL FIELD

The present invention generally relates to a methods and systems for determining risk of defect related semiconductor device failure, and more particularly to determining risk of defect related semiconductor device failure utilizing design data.

BACKGROUND

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etching, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Accordingly, much work in the inspection field has been devoted to designing inspection systems that can detect defects having sizes that were previously negligible. Typical inspection processes detect defects by comparing similar semiconductor device areas on a wafer. The differences detected between the two device areas can either be a defect, which can cause a device to function improperly, or a nuisance, which will not affect system operations. An integral phase of semiconductor wafer inspection involves optimizing the settings, commonly referred to as the "recipe," of an inspection device so that it can accurately distinguish defects from nuisances. After potential defects are found by an inspection system, the wafer is typically transferred to a review tool for classification of the defects. However, classification of the defects requires optimizing the settings of the review tool, also referred to as a "recipe", so that the review tool can adequately classify the potential defects or determine that the potential defects are nuisances or false defects. In sum, analysis of the defects on a particular wafer lot requires setting up and optimizing a recipe for an inspection tool and setting up a different recipe for the review tool. Setting up two recipes for two different tools is time consuming and complex.

Inspection for many different types of defects has also become more important recently. For instance, in order to use inspection results to monitor and correct semiconductor fabrication processes, it is often necessary to know what types of defects are present on a wafer. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Defect review typically involves generating additional information about defects at a higher resolution using either a high magnification optical system or a scanning electron microscope (SEM). The higher resolution data for the defects generated by defect review is more suitable for determining attributes of the defects such as profile, roughness, more accurate size information, etc. Defect analysis may also be performed using a system such as an electron dispersive x-ray spectroscopy (EDS) system. Such defect analysis may be performed to determine information such as composition of the defects. Attributes of the defects determined by inspection, review, analysis, or some combination thereof can be used to identify the type of the defect (i.e., defect classification) and possibly a root cause of the defects. This information can then be used to monitor and alter one or more parameters of one or more semiconductor fabrication processes to reduce or eliminate the defects.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects and nuisance defects detected by inspection grows dramatically. Therefore, more and more defects may be detected on the wafers, and correcting the processes to eliminate all of the defects may be difficult and expensive. As such, determining which of the defects actually have an effect on the performance of the devices and the yield may allow process control methods to be focused on those defects while largely ignoring others. Furthermore, at smaller design rules, process induced failures may, in some cases, tend to be systematic. That is, process induced failures tend to fail at predetermined design patterns often repeated many times within the design. Elimination of spatially systematic, electrically relevant defects is important because eliminating such defects can have a significant overall impact on yield. Whether or not defects will affect device parameters and yield often cannot be determined from the inspection, review, and analysis processes described above since these processes may not be able to determine the position of the defect with respect to the electrical design

SUMMARY

A method for design based assessment of a device is disclosed. In one aspect, a method may include, but is not limited to, defining a plurality of patterns of interest utilizing design data of the device; generating a design based classification database, the design based classification database including design data associated with each of the patterns of interest; receiving one or more inspection results; comparing the one or more inspection results to each of the plurality of patterns of interest in order to identify an occurrence of at least one of the patterns of interest in the inspection results; determining yield impact of each pattern of interest utilizing process yield data; monitoring a frequency of occurrence of each of the POIs and the criticality of the POIs in order to identify one or more process excursions of the device; and determining a device risk level by calculating a normalized polygon frequency for the device utilizing a frequency of occurrence for each of the critical polygons and a criticality for each of the critical polygons, the critical polygons defined utilizing design data of the device.

A method for providing dynamic sampling utilizing critical defects is disclosed. In one aspect, a method may include, but is not limited to, identifying a plurality of critical pattern types on a wafer; determining a device risk level utilizing a calculated risk level and frequency of occurrence for each of the identified critical pattern types; identifying one or more relevant excursions of the device; determining dynamic wafer selection in response to the identification of one or more device excursions; and dynamically sampling at least some of the identified critical pattern types.

A method for method for providing risk assessment or yield correlation in a memory device is disclosed. In one aspect, a method may include, but is not limited to, defining a plurality of regions based on one or more functional areas of a device utilizing design data; performing one or more inspection processes on the one or more defined regions; identifying one or more dies of the one or more defined regions falling below a predetermined control limit utilizing inspection data from the one or more inspection processes; and identifying regions impacting yield loss by comparing the one or more dies falling below the predetermined control limit to inline data for each of the regions.

A method for monitoring device processing using spatial analysis is disclosed. In one aspect, a method may include, but is not limited to, monitoring a process variation signature by inspecting one or more devices between one or more process steps; associating one or more patterns of interest of the one or more devices with a monitored process variation using a design based classification process; and identifying one or more equipment signatures using the one or more associated patterns of interest.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
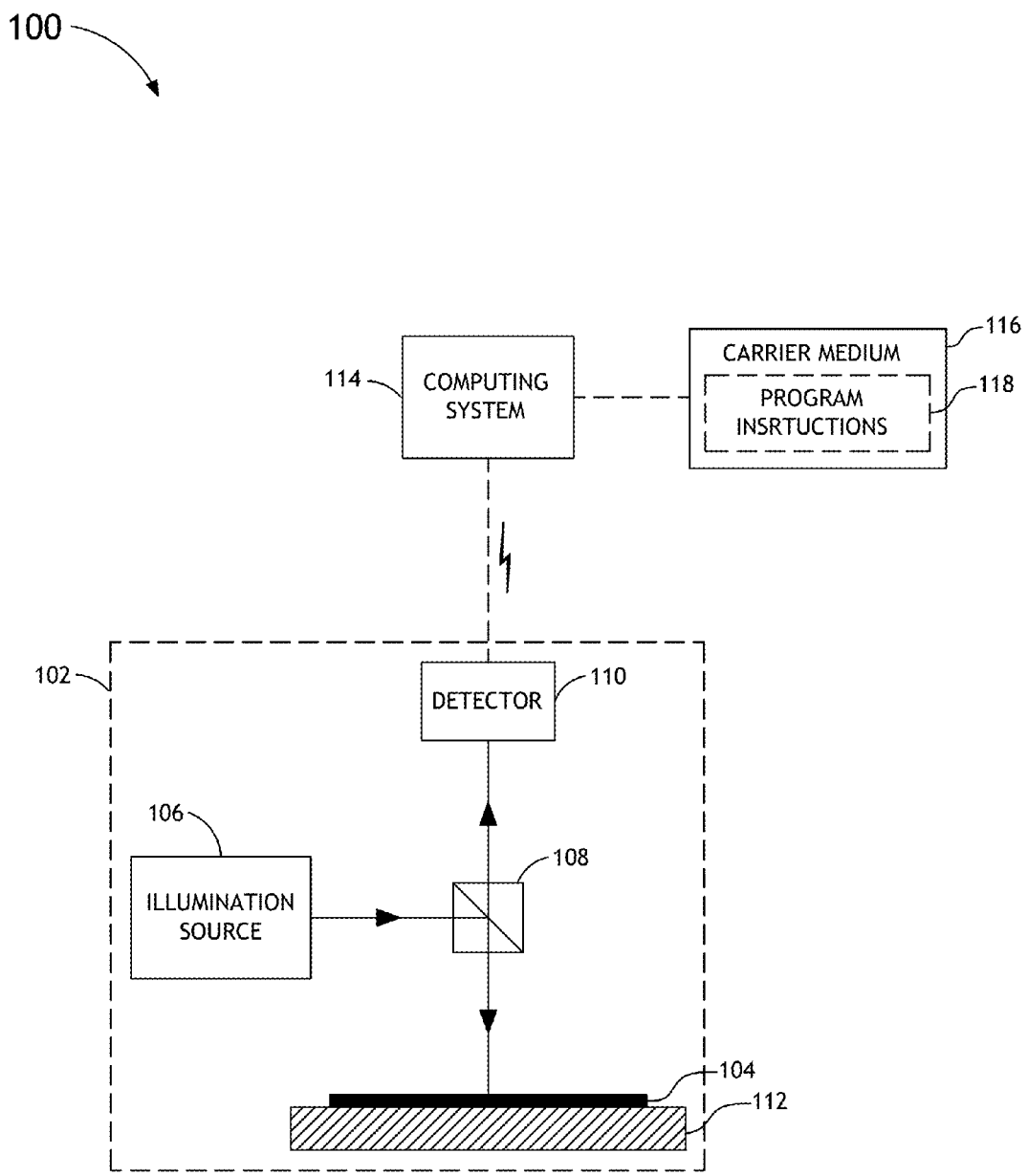
FIG. 1A illustrates a block diagram view of a system suitable for semiconductor wafer inspection, in accordance with one embodiment of the present invention.

Reference will now be made in detail to the subject matter disclosed, which is illustrated in the accompanying drawings.

Referring generally to FIGS. 1A through 9, a method and system for design based device assessment are described in accordance with the present disclosure. The present invention is directed to predictive monitoring of systematic defects as well as risk level assessment of defects in a device (e.g., semiconductor device). As described in greater detail further herein, risk level assessment of a device is achieved utilizing a novel polygon frequency (NPF) involving the analysis of critical polygons defined within he design data of a given device. Moreover, the utilization of pattern grouping with typical random defectivity may aid in separating systematic defect occurrences from random particle occurrences. The present disclosure provides for design-aware defect inspection through design layout pattern search capabilities, accurate inspection area definition, and an understanding of the printed frequency of relevant structures present in the design data of a device. The present disclosure is directed to i) providing design based risk assessment of a device; ii) providing dynamic sampling using critical defect information; iii) determining memory device risk assessment and/or yield correlation in a memory device; and iv) monitoring device processing using spatial analysis.

As used throughout the present disclosure, the term "wafer" generally refers to substrates formed of a semiconductor or non-semiconductor material. For example, a semiconductor or non-semiconductor material include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for improved defect detection for overlay error of semiconductor target such as a reticle, which may also be commonly referred to as a mask or a photo mask. Many different types of reticles are known in the art, and the terms "reticle," "mask," and "photo mask" as used herein are intended to encompass all types of reticles known in the art.

A semiconductor chip design known as the "floorplan" contains the placement information for repeating structures known as cells. This information can be extracted from the physical design of a chip usually stored in GDSII or OASIS file formats. The structural behavior or process-design interactions can be a function of the context (surroundings) of a cell. By using the floor plan, the analysis proposed can automatically tell which cell types are having problems, what the location within the cell is (coordinates of the polygons having problems) and the context (what are the adjacent cells) in which the cell is having problems if this is a factor.

Each defect found by an inspector for a given wafer would be subjected to the standard cell repeater analysis which is typically done at the die and reticle level. Conventionally repeater analysis is performed across die, across reticle across wafer and wafer to wafer spatial analysis on cell defectivity to identify the signature of die, reticle, wafer and process equipment level phenomenon that interact with the weak structures that are sensitive to process variations.

In other embodiments, an image of a reticle generated by a reticle inspection system is used as design data in the design data space. The reticle is used to print the design data on the wafer. In this manner an image beam image of the reticle is acquired by a high magnification optical reticle inspection system or an electron beam based reticle inspection system respectively. Alternatively the image of the reticle may be an aerial image of the reticle acquired by an aerial imaging reticle inspection system. The image of the reticle may be used as a proxy for the design data in any of the embodiments described herein that use design data to perform one or more steps.

The term "design data" as used in the present disclosure generally refers to the physical design of an integrated circuit and data derived from the physical design through complex simulation or simple geometric and Boolean operations. In addition, an image of a reticle acquired by a reticle inspection system and/or derivatives thereof may be used as a proxy or proxies for the design data. Such a reticle image or a derivative thereof may serve as a substitute for the design layout in any embodiments described herein that uses design data. Design data and design data proxies are described in U.S. Pat. No. 7,676,007 by Kulkarni issued on Mar. 9, 2010; U.S. patent application Ser. No. 13/115,957 by Kulkarni filed on May 25, 2011; U.S. Pat. No. 8,041,103 by Kulkarni issued on Oct. 18, 2011; and U.S. Pat. No. 7,570,796 by Zafar et al. issued on Aug. 4, 2009, all of which are incorporated herein by reference.

Figure 1B:
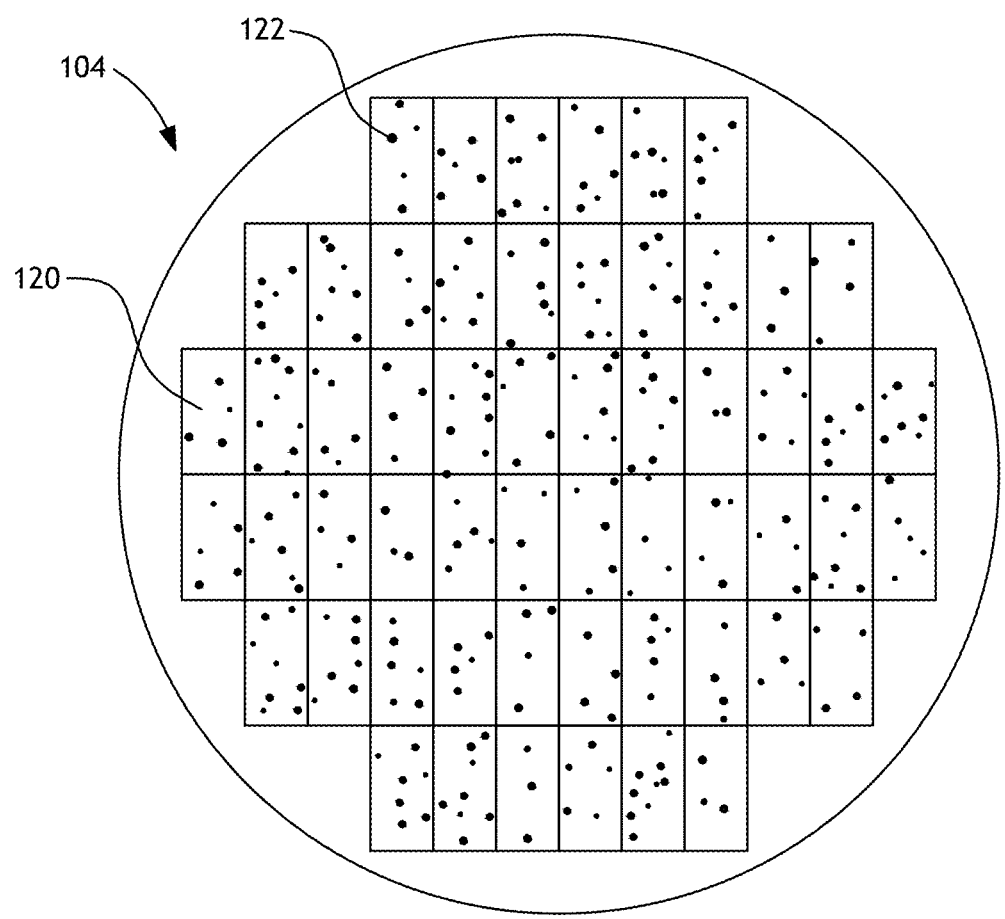
FIG. 1B illustrates a top plan view of a semiconductor wafer having multiple die regions and multiple defects within the die regions, in accordance with one embodiment of the present invention.

FIGS. 1A and 1B illustrate an inspection system 100 which may be utilized to perform the various processes described further herein. In one aspect, the system 100 may include an inspection tool 102 configured to detect defects on a semiconductor wafer 104 disposed on a sample stage 112. The inspection tool 102 may include any appropriate inspection system known in the art, such as, but not limited to, a bright-field inspection system, a dark-field inspection system, or an electron beam inspection system. In a further aspect, the inspection tool 100 may include an illumination source 106, a beam splitter 108, and a detector 110.

The illumination source 106 may include any illumination source known in the art. For example, the illumination source 106 may include a narrow band light source, such as a laser source. In a further embodiment, the illumination source 104 may be configured to direct light to the beam splitter 108. In turn, the beam splitter 108 may be configured to direct light from the illumination source 106 to the surface of the wafer 104 disposed on the sample stage 112. Further, the beam splitter 108 may be configured to transmit light reflected from wafer 104 to the detector 110.

The detector 110 may include any appropriate detector known in the art. In one embodiment, the detector 110 may include a charge coupled device (CCD) camera. The detector 110 may be used to detect actual defects (e.g., defects 122) on wafer 104. In a further embodiment, the output of the detector 110 may be communicatively coupled to the one or more computing systems 114. In this regard, the one or more computing systems 114 may be configured to detect actual defects on wafer 104 using detection data collected and transmitted by the detector 110. The one or more computing systems 108 may utilize any method and/or algorithm known in the art to detect defects on the wafer. Those skilled in the art should recognize that the inspection tool 102 may be utilized to detect defects distributed across the semiconductor wafer. For example, as shown in FIG. 1B, the wafer 104 may include multiple defects distributed across multiple dies 120 of the wafer 104.

Further, the one or more computing systems 110 may be coupled to the detector in any suitable manner (e.g., by one or more transmission media indicated by the dotted line shown in FIG. 1, which may include any suitable transmission media known in the art) such that the computer system can receive the output generated by the detector. Furthermore, if the inspection tool 102 includes more than one detector (not shown), the one or more computing systems 110 may be coupled to each detector as described above. In a further embodiment, the wafer 104 may be disposed on a sample stage 112. The sample stage 112 may include any appropriate mechanical and/or robotic assembly known in the art.

In a further embodiment, the inspection tool 102 may be configured to accept instructions from another subsystem of the system 100 in order to dynamically identify defects of the semiconductor wafer 104. For instance, the inspection tool 102 may accept instructions from one or more computing systems 114 of the system 100. Upon receiving the instructions from the one or more computing systems 114, the inspection tool 104 may perform an inspection process at the locations of the semiconductor wafer 104 identified in the provided instructions. The one or more computing systems 110 may be configured to perform any other step(s) of any of the method embodiments described herein.

In another embodiment, the one or more computing systems 110 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the one or more computing systems 110 and other subsystems of the system 100. Moreover, the one or more computing systems 110 may send data to external systems via a transmission medium.

The one or more computing systems 110 may include, but are not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 118 implementing methods such as those described further herein may be transmitted over or stored on carrier medium 116. The carrier medium 116 may be a transmission medium such as a wire, cable, or wireless transmission link. The carrier medium 116 may also include a storage medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step (s) of any of the method embodiment(s) described herein.

Figure 2:
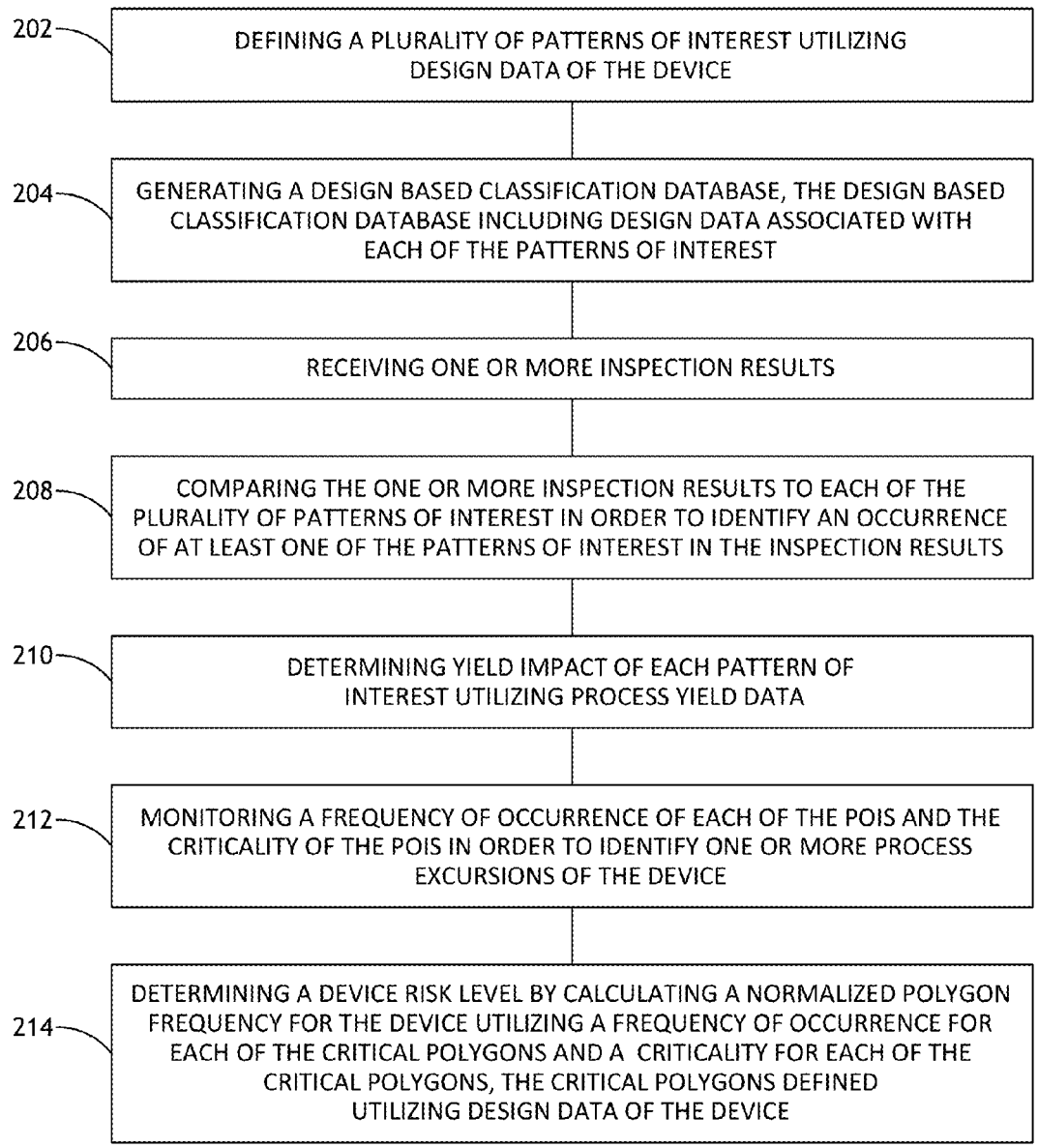
FIG. 2 is a flow diagram illustrating a method for design based device assessment, in accordance with one embodiment of the present invention.

FIG. 2 is a flow diagram illustrating steps performed in a computer-implemented method 200 for design based device assessment.

In a first step 202, a plurality of patterns of interest may be defined utilizing design data associated with a wafer. It is noted herein that each of the identified POIs may possess a level of criticality relative to performance of the given device. In some embodiments, the multiple POIs may be identified on the semiconductor wafer utilizing data from electronic design automation (EDA) tools and other knowledge. Any such information about the design generated by an EDA tool may be used to identify multiple POIs. For example, the POIs may be selected as a pattern that form part of a critical path or is located at or near a critical path on the same layer as the POI or on another layer of the wafer. In addition, the design data may be searched for one or more POIs in any suitable manner. For example, searching the design data for one or more POIs may be performed as described in the above-referenced patent applications by Kulkarni et al. and Zafar et al., which are incorporated by reference. In addition, the POI(s) may be selected or identified using any other method or system described in this patent application. In a further embodiment, the multiple POIs may be identified utilizing a design rule checking (DRC) process, an optical rule checking (ORC), or a failure analysis (FA) process in order to identify patterns critical to device performance. In another embodiment, the multiple POIs may be identified utilizing a process window qualification method (PWQ). Searching design data for one or more POIs may be performed as described in the above-described references by Kulkarni et al. and Zafar et al., which are incorporated above by reference above. In addition, the POI(s) may be selected or identified using any other method or system described in these patent applications.

In a second step 204, a design based classification (DBC) database may be generated. In one aspect, the DBC database includes design data associated with each of the patterns of interest critical to the performance of the given device. For example, the DBC database may incorporate design data stored in a data structure such as a graphical data stream (GDS) file. A GDSII file is one class of files used for the representation of design layout data. Other types of files may include GLI and OASIS files. In a further aspect, upon identification of the POIs, the DBC database may be formed utilizing a design based binning (DBB) process. The utilization of GDS file types and design based binning are generally described in the references by Kulkarni et al. and Zafar et al., which are incorporated by reference above. In a general sense, the system 100 (e.g., via the one or more computing systems 110) may generate a DBC database, or library, which includes noteworthy pattern types along with the corresponding spatial coordinates (e.g., X-Y coordinates) of those patterns, along with specific designs.

In a further aspect, the DBC database may include a criticality factor or 'weight' associated with each POI defined in step 302. In some embodiments, the 'weight' of the criticality associated with each of the POIs is determined utilizing test data, such as, but not limited to, data associated with logic/memory portions of the wafer, functional tests, failure analysis (FA) and the like. As will be described further herein, the criticality factor associated with the patterns along with the frequency of occurrence of the patterns in the given device may be used to determine a relative risk level of failure for a given die or an entire device.

In a third step 206, one or more inspection results may be received. In one aspect, one or more inspection results from the detector 110 of the inspection tool 102 may be received by the one or more computing systems 114. The inspection results received by the one or more computing systems 114 may include any type of inspection data known in the art. For example, the inspection data may include, but is not limited to, bright field (BF) inspection data or dark field (DF) inspection data. In a fourth step 208, the one or more inspection results acquired in step 206 may be compared to each of the POIs of the DBC library in order to monitor for occurrences of the critical POIs.

In a fifth step 208, a yield impact of each pattern of interest may be determined using end-of-line yield data. In this regard, the criticality of each pattern of interest may be quantified by analyzing the impact the given pattern has on the end-of-line yield. As previously noted, each pattern of interest possesses a different criticality. In order to access the relative criticality of a given pattern of interest, the pattern type may be assessed using test data (e.g., logic testing, memory testing, functional testing, FA, and the like). Further, criticality can be determined systematically utilizing design pattern grouping, allowing the system to determine criticality without the need of defect classification, as required in the prior art.

Figure 3:
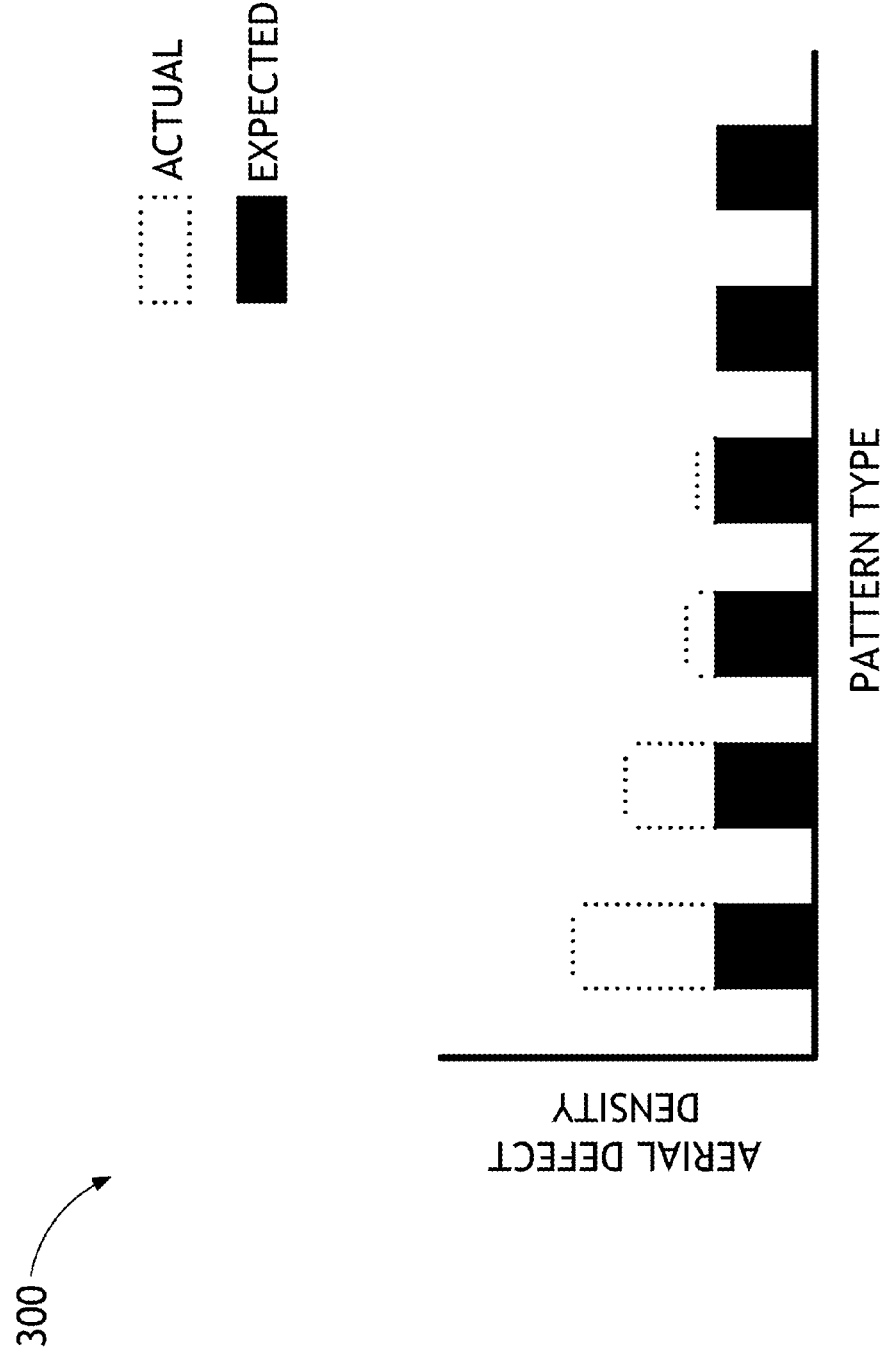
FIG. 3 illustrates a Pareto chart utilized to identify one or more excursions of a device, in accordance with one embodiment of the invention.

In a sixth step 210, a frequency of occurrence and criticality of each of the patterns of interest may be monitored in order to monitor the device for device excursion. In one embodiment, the criticality associated with each pattern of interest along with the frequency of occurrence of the given pattern of interest may be monitored and displayed in a normalized Pareto chart. FIG. 3 illustrates a weighted Pareto chart 300 illustrating the aerial defect density as function of the pattern type. The shaded bars indicate the expected level of defect density, while the white bars indicate the actual defect density. For instance, a typical Pareto chart in this context may illustrate the GDS pattern group ID along the x-axis and the defect count along the y-axis. In a general sense, the Pareto chart graphically illustrates the number of defects binned into each of the different groups, each of which corresponds to a different portion of the GDS pattern. Those skilled in the art should further recognize that a device excursion is commonly indicated when the ratio between the actual and expected defect density is higher than a typical value. The use of excursion analysis using Pareto charts is described in U.S. Pat. No. 7,975,245 by Florence issued on Jul. 5, 2011, which is incorporated herein by reference.

Figure 4:
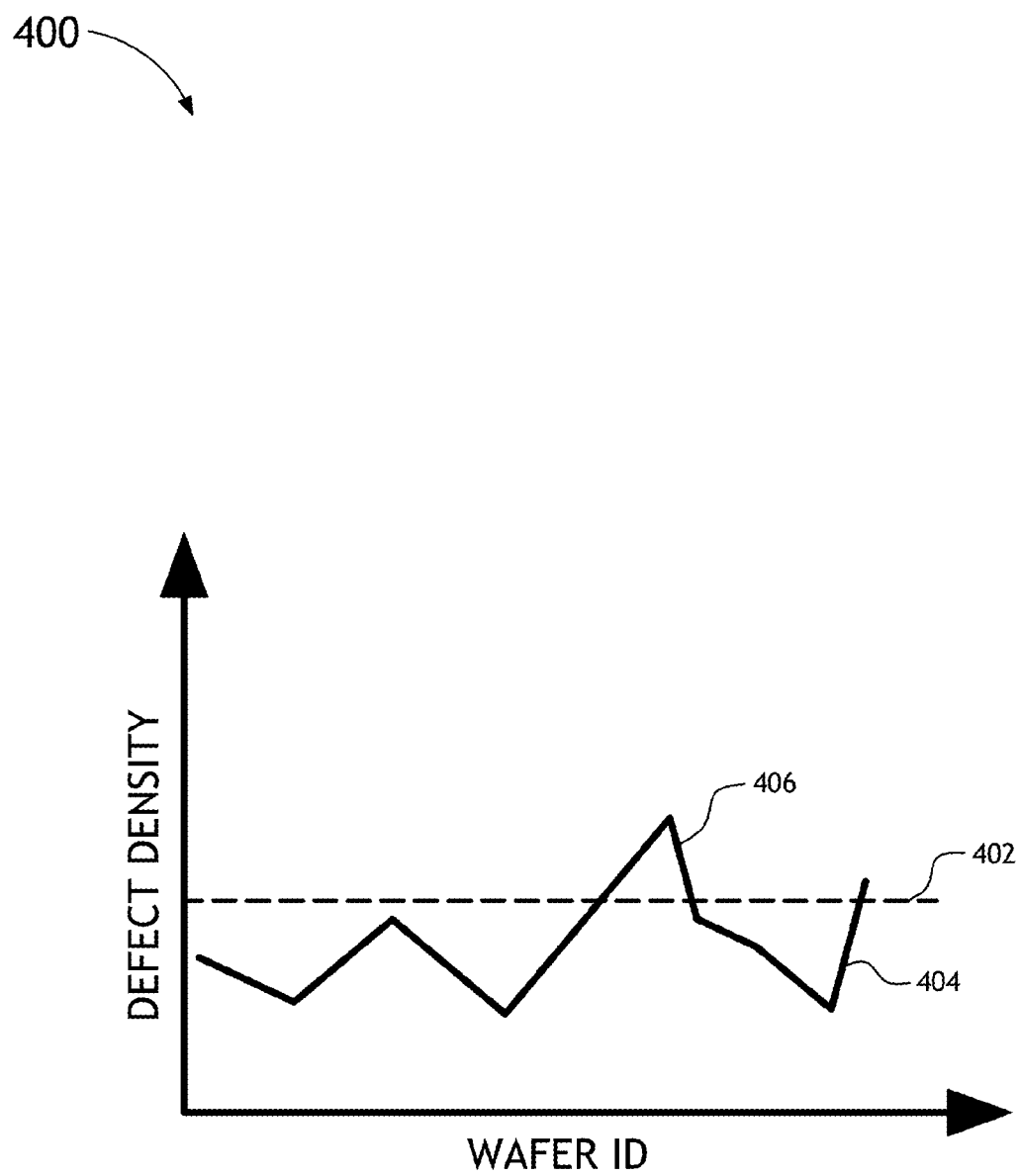
FIG. 4 illustrates a trendline generated via a statistical process control routine utilized to identify one or more excursions of a device, in accordance with one embodiment of the present invention.

FIG. 4 illustrates a set of Statistical Process Control (SPC) data 400 illustrating the defect density as a function of pattern type. The data 400 in FIG. 4 represents a weighted trend chart 404 generated over a period time for a given bin created utilizing the criticality of each POI. Utilizing this type of analysis process, excursion 406 exceeding a typical defect density level 402 involving process tool variation may be analyzed via process tool commonality. For instance, KLAR-ITY produced by KLA-TENCOR is suitable for analyzing process excursion issues involving process tool variation may be analyzed via process tool commonality. It is noted herein that the present method and system of this disclosure allows for the creation of the SPC chart 400 using the weighted criticality values associated with the various patterns of interest.

In a seventh step 212, a device risk level may be determined by calculating a normalized polygon frequency for the device utilizing a frequency of occurrence of each of the critical polygons and a criticality for each of the critical polygons. In one aspect, the critical polygons of the design data associated with the device are determined utilizing a design based search algorithm. In one embodiment, the design based classification algorithm of the present invention may identify one or more polygons in the design data of the device on which the critical patterns are located. As such, the spatial analysis of the critical polygons found in step 212 may be indicative of the overall device risk of the device created by the physical defects found in the device. In a further embodiment, the system 100 may generate a frequency table containing the frequency of occurrence of each polygon type along with the corresponding risk level associated with each polygon type.

Figure 5:
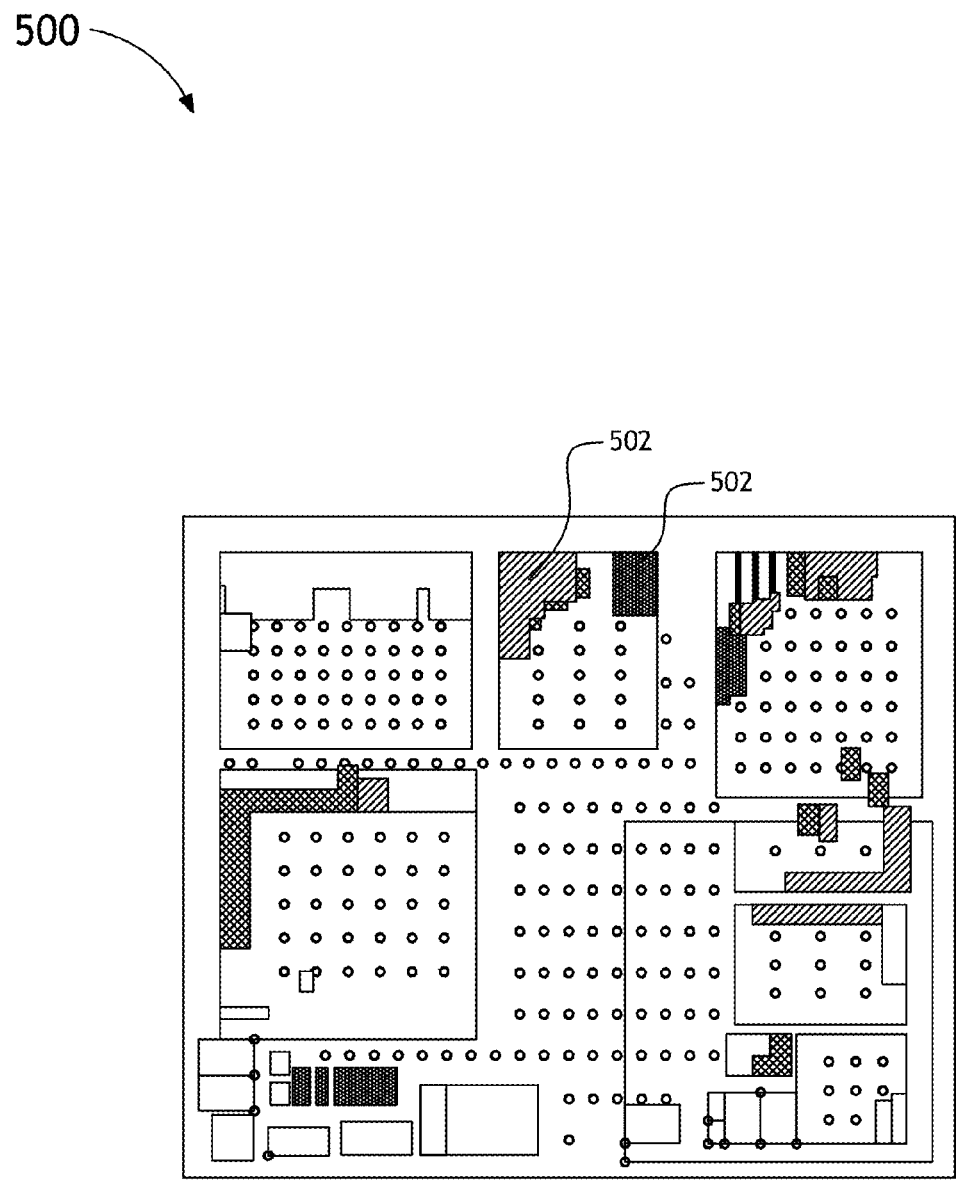
FIG. 5 illustrates multiple critical polygons of device design data, in accordance with one embodiment of the present invention.
Figure 6:
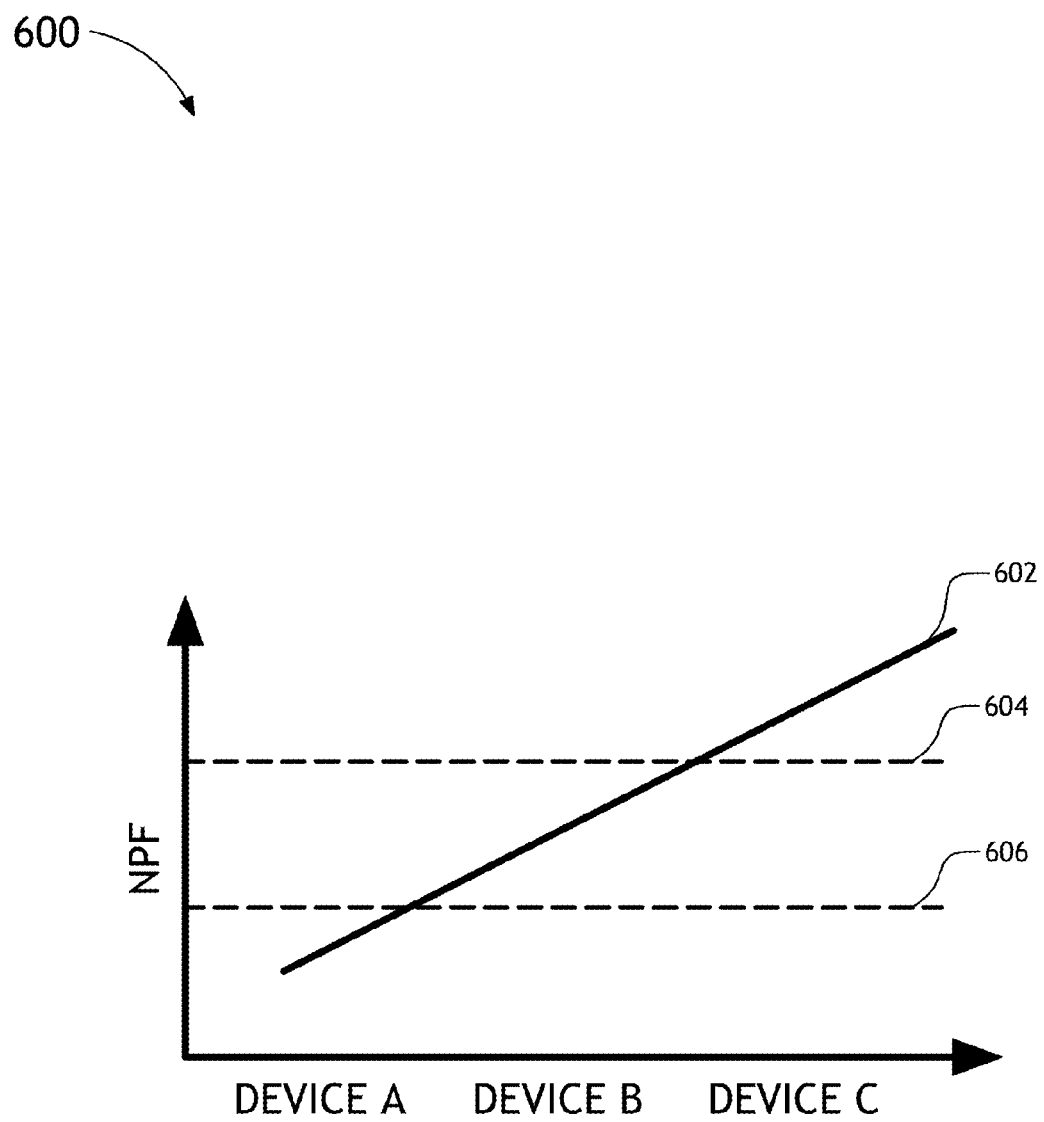
FIG. 6 illustrates normalized polygon frequency for a variety of devices, with superposed recommendation thresholds, in accordance with one embodiment of the present invention.

In a further embodiment, physical FA or DRC may both be utilized by the system 100 in order to determine the size, position, and frequency of the critical polygons. In another aspect, a simulation process may be utilized to determine the critical polygons. Utilizing one or more design files of the system 100, a detailed inspection area may be generated allowing for improved inspection tuning and binning, along with the placement of the critical polygons in the various blocks of the design layout. FIG. 5 illustrates a conceptual view of the critical polygons of the present invention. As shown in FIG. 5, multiple polygon types 502 may be utilized. In this manner, at least a portion of the critical polygons may be located proximately to the critical patterns identified in the previous steps of the present method. The implementation of polygons using the design data of a device is generally described in U.S. patent application Ser. No. 12/534,547 by Zafar filed on Aug. 3, 2009, which is incorporated herein by reference.

In a further aspect, the system 100 may determine an overall device risk level utilizing the identified critical polygons. In this manner, the one or more computing systems 110 of the system 100 may calculate a normalized polygon frequency for the device utilizing the frequency of occurrence and the criticality associated with each individual critical polygon identified using the design data. It is noted herein that as the number of critical polygons increase in size and/or criticality the overall risk of failure due to the presence of critical defects (correlated with the critical polygons) will also increase. For example, an observed high level of critical polygons represents a device having a high probability of chip failure.

The device level risk of failure may be expressed as:

$$DLR \approx NPF = 100 \times \sum_{i}^{\infty} \frac{f_i^p}{A_i} \quad \text{Eq. 1}$$

Where DLR represents device level risk, NPF represents normalized polygon frequency, $f^p$ represents the polygon frequency for each type of polygon, and A represents the area of each polygon type. In this regard, the device level risk calculated utilizing the normalized polygon frequency algorithm represents a pattern failure index, which may be used to assess the risk of failure of each device as a result of one or more critical patterns. In this manner, the generated frequency table allows for the evaluation of device risk level that may be assigned in terms of the sensitivity against process variation involving systematic yield loss. In general sense, the above description should not be interpreted as a limitation. It is contemplated herein that the normalized polygon frequency algorithm may be extended to any number of polygons and polygon shapes. Moreover, the correlation function between the actual device level risk and the calculated normalized polygon frequency may take on any suitable form.

In a further embodiment, upon detecting a NPF chart indicating a high level of critical polygon, foundry users may determine whether to tight process specification (e.g., overlay, critical dimension, thickness, process tool factor, and the like) or to modify DFM rules to reduce potential yield loss. FIG. 5 illustrates a conceptual view of NPF across a function of devices, along with selectable thresholds for determining what course of action to take for high NPF devices. The threshold for optimizing the process specification and the threshold for optimizing design on the DFM are indicated by dotted lines 506 and 504 respectively. The trendline 502 indicates the status of the represented devices, Device A, Device B, and Device C. For instance, in the case of Device A, which displays a relatively low NPF (and thus is at lower risk of failure), the selected thresholds may lead the system 100 (e.g., system implementing foundry fab software) to provide feedback to a foundry use for appropriate action. For example, in the case of Device A of FIG. 5, the system 100 may provide a recommendation to the user to optimize process specification. By way of another example, in the case of Device B, the system 100 may provide a recommendation to the user to optimize device design on DFM.

Figure 7:
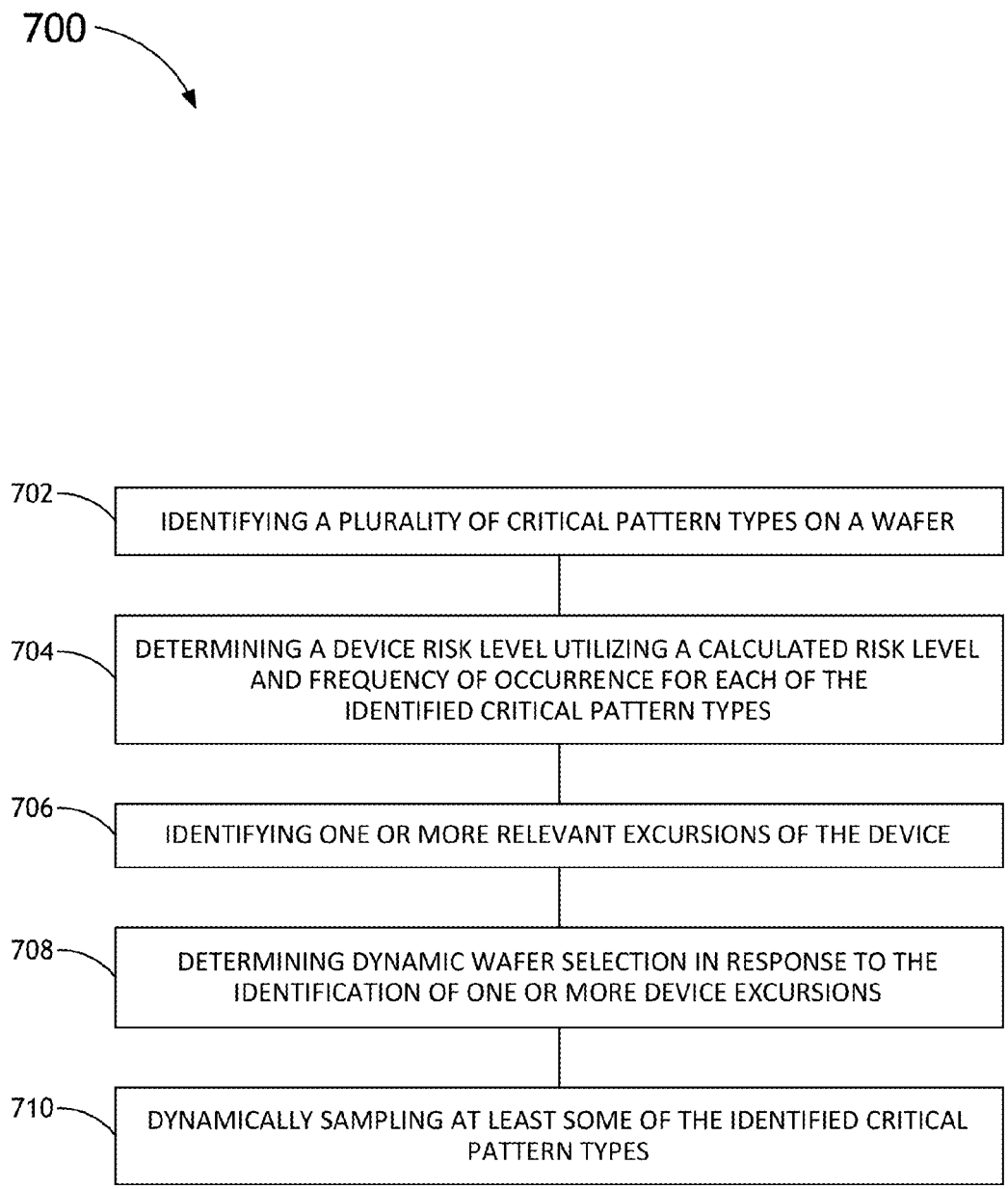
FIG. 7 is a flow diagram illustrating a method for dynamic sampling, in accordance with one embodiment of the present invention.

FIG. 7 is a flow diagram illustrating steps performed in a computer-implemented method 700 for providing dynamic sampling utilizing critical defects. Applicant notes that the embodiments and enabling technologies described previously herein in the context of flow diagram 200 should be interpreted to extend to method 700.

In a first step 702, a plurality of critical pattern types on a wafer may be identified. In one embodiment, multiple critical patterns on a device may be identified utilizing the criticality, or significance, of each pattern type to device performance or yield loss. In this regard, upon identifying multiple defects, the computing system 110 of the system 100 may group together multiple defects into a particular pattern type. Utilizing the multiple patterns the system 100 may further provide a relative risk level (see method 200 for more details) associated with each pattern for a given die or the entire wafer.

In a second step 704, a device risk level may be determined utilizing a calculated risk level and frequency of occurrence for each of the indentified critical pattern types, or patterns of interest. In a third step 706, one or more excursions of the device may be identified. In this regard, relevant excursions may be identified utilizing the risk level and the frequency of occurrence associated with each of the critical pattern types. For example, when the defect density associated with a given pattern type exceeds a predetermined criteria the system 100 may identify the instance as a device excursion. For instance, a Pareto chart, similar to that illustrated in FIG. 3 may be used to identify relevant excursions. Utilizing the analysis information of each pattern of interest a risk index may be determined for each die of a wafer. Based on the determined risk index, a signal may be transmitted to a user (e.g., design user) indicative of a recommendation as to whether to consider making changes to the process conditions, or, at a minimum, to anticipate reduce yield.

In a fourth step 708, in response to the identification of one or more device excursions, a dynamic wafer selection may be determined. In this regard, it is contemplated herein that once excursions are detected utilizing the critical POIs a user might seek to increase the wafer selection. In a fifth step 710, one or more of the identified critical pattern types may be dynamically sampled. In one embodiment, the amount of defect sampling may change in proportion to the number of critical pattern occurrences. As such, as a particular critical pattern increasing in occurrence frequency relative to other pattern types the higher occurring pattern will be sampled at a higher rate. In another embodiment, the system 100 may be adjust to keep the sampling rate for high frequency patterns at a relatively low rate in order to allow sampling of lower frequency defects. This is particularly advantageous when sampling budgets are present.

Figure 8:
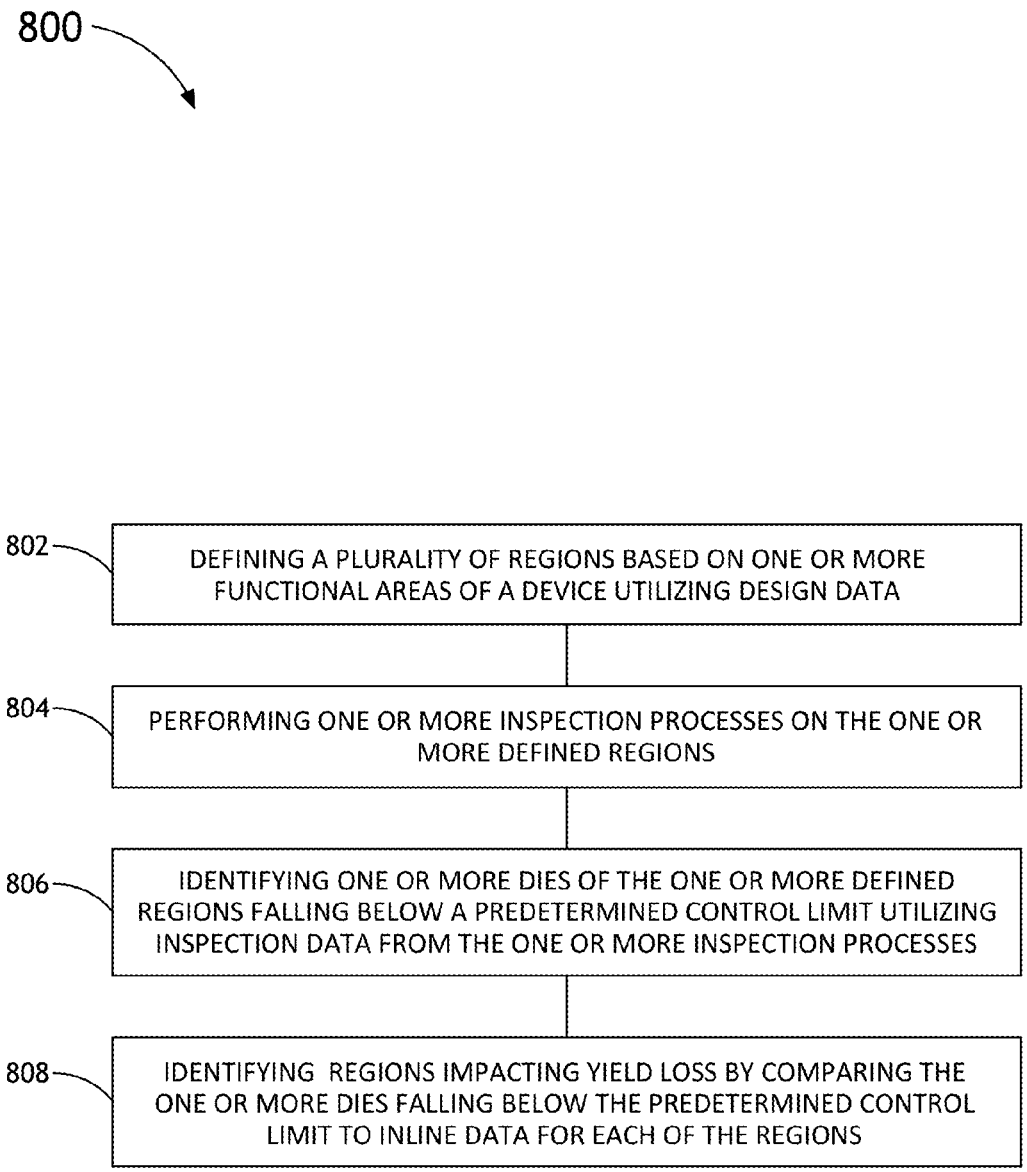
FIG. 8 is a flow diagram illustrating a method for determining yield correlation in a memory device, in accordance with one embodiment of the present invention.

FIG. 8 is a flow diagram illustrating steps performed in a computer-implemented method 800 for determining yield correlation in a memory device. Applicant notes that the embodiments and enabling technologies described previously herein in the context of flow diagram 200 should be interpreted to extend to method 800. It is noted herein that not all device yield loss is related to the presence of defects that are not defined by their criticality of regions. For example, a defect in a redundancy area may have no impact on yield, while a defect in an SA area may display a high impact on device yield. The following method incorporates the use of design data to set up a precise inspection area definition and to aid in correlating design data with yield data for finer resolution in killed die analysis. Use of design data allows for finer separation between areas on a device (e.g., main area and redundancy area) while also allowing cosmetic defects to be distinguished high impact defects.

In a first step 802, a plurality of regions based on one or more fundamental areas of a device may be defined utilizing design data. In some embodiments, the regions may be based on at least one of a main area of the device, a SA area, a redundant memory area of the device, or a dummy area of the device. In a second step 804, one or more inspection measurements may be performed on the regions defined in step 802. For example, the inspection process may include any inspection process known in the art, such as dark field inspection or bright field inspection. In a third step 806, one or more dies of the one or more defined regions falling below a predetermined control limit may be identified utilizing the inspection data collected in step 804. In this regard, a user may establish a control limited based on an expected defect frequency in one or more dies. In a fourth step 808, regions impacting yield loss may be identified by comparing the one or more dies falling below the predetermined control limit to inline data or each of the regions. In this regard, the system 100 may identify and bin die based on the die roll-up using the critical pattern of interest. In contrast to a defect density or defect count per die, it is contemplated herein that a die index configured to determine the risk associated with each die.

Figure 9:
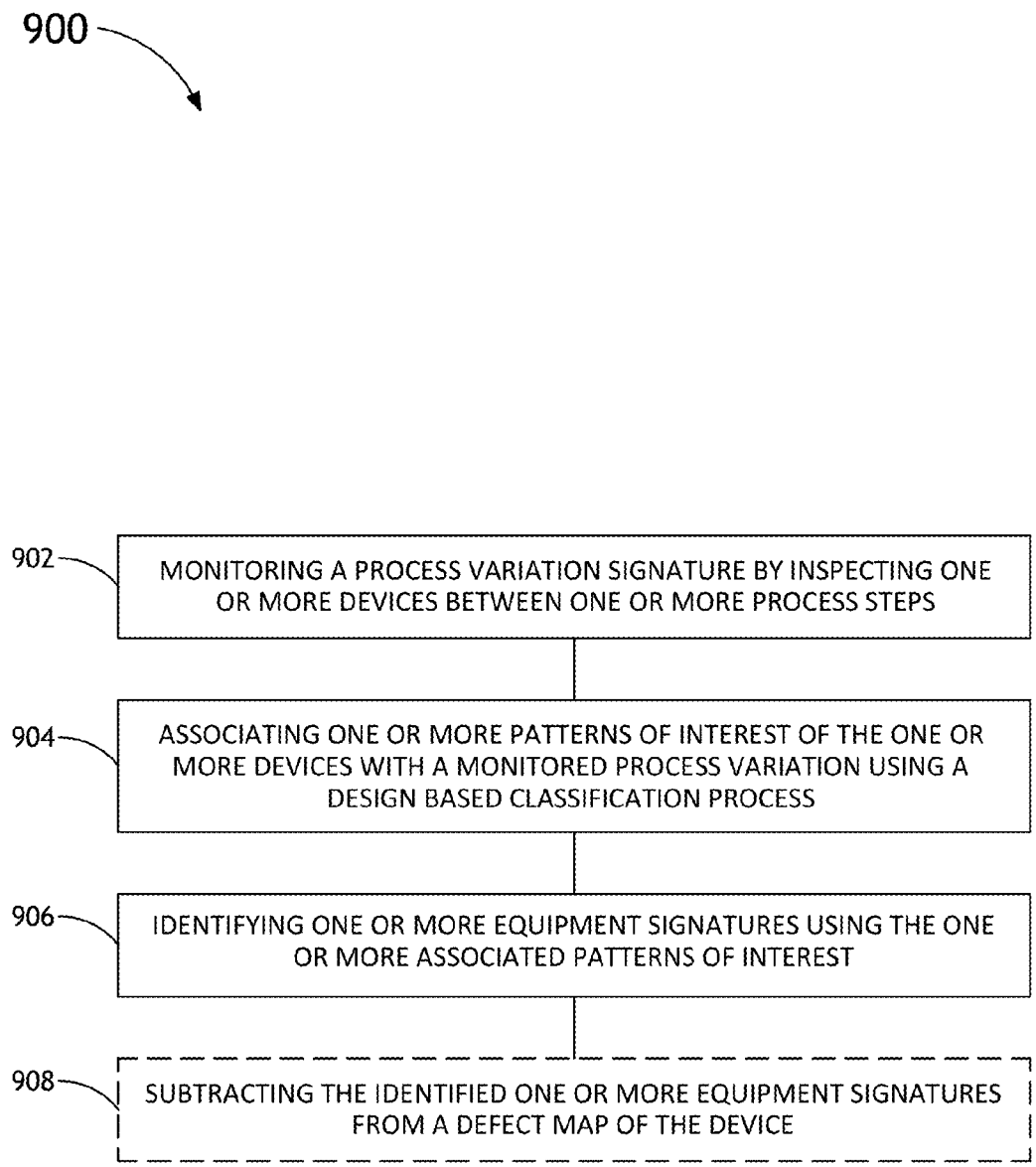
FIG. 9 is a flow diagram illustrating a method for monitoring device processing using spatial analysis, in accordance with one embodiment of the present invention.

FIG. 9 is a flow diagram illustrating steps performed in a computer-implemented method 900 for monitoring device processing using spatial analysis. Applicant notes that the embodiments and enabling technologies described previously herein in the context of flow diagram 200 should be interpreted to extend to method 900. It is noted herein that device processing equipment often experiences failure or process variation signatures due to various factors, such as, but not limited to, etch rate difference, plasma pattern within the chamber, exhaust and gas flow pattern, and temperature variations. These types of variances result in pattern failure and/or noise level changes. Analysis of the spatial signal of the variation may be used to monitor process, filter out noise, or to isolate process tool failure.

In a first step 902, a process variation signature may be monitored by inspecting one or more devices between one or more process steps using an inspection tool. In a second step 904, one or more patterns of interest of the device may be associated with a monitored process variation using a design based classification process. In a third step 906, one or more equipment signatures may be identified by the system 100 using the associated patterns of interest found in step 904. In a further step 908, the one or more equipment signatures may be used to subtract from an acquired defect map. In this regard, the equipment signature may be removed from the defect map, thus isolating the defect patterns present in the defect map. This correction allows the system 100 to remove systematic equipment signatures, improving the overall defect data.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A method for providing risk assessment or yield correlation in a memory device, comprising:
    defining a plurality of regions based on one or more functional areas of a device as identified in design data of the device;
    performing one or more inspection processes on the one or more defined regions;
    identifying one or more dies of the one or more defined regions falling below a predetermined control limit by analyzing the inspection data from the one or more inspection processes to determine whether a defect frequency of the one or more defined regions of the one or more dies is below the predetermined control limit; and
    identifying regions impacting yield loss by comparing the one or more dies falling below the predetermined control limit to inline data for each of the regions.

2. The method of claim 1, wherein the one or more functional areas of the memory device comprise:
    at least one of a main area of the memory device, a redundant memory area of the memory device, and a dummy area of the memory device.

3. The method of claim 1, wherein the one or more inspection processes comprise:
    at least one of dark field inspection and bright field inspection.

4. The method of claim 1, wherein the predetermined control limit is user established.

* * * * *